(12) United States Patent
Raston et al.

(10) Patent No.: US 8,365,923 B2
(45) Date of Patent: Feb. 5, 2013

(54) METHODS FOR SELECTIVELY SEPARATING CARBON NANOTUBES

(75) Inventors: Colin Llewellyn Raston, Mandurah (AU); Lee John Hubble, Sydney (AU)

(73) Assignee: The University of Western Australia, Crawley, WA (AU)

( * ) Notice: Subject to any disclaimer, the term of this patent is extended or adjusted under 35 U.S.C. 154(b) by 679 days.

(21) Appl. No.: 12/610,169

(22) Filed: Oct. 30, 2009

(65) Prior Publication Data

US 2010/0166624 A1    Jul. 1, 2010

(30) Foreign Application Priority Data

Oct. 31, 2008 (AU) ................................ 2008905620
Dec. 5, 2008 (AU) ................................ 2008906319

(51) Int. Cl.
    *C01B 31/02* (2006.01)
    *B82B 3/00* (2006.01)
    *B03B 1/04* (2006.01)

(52) U.S. Cl. ............... 209/162; 209/2; 209/4; 209/172; 209/233; 423/445 R; 423/445 B; 423/461; 977/745; 977/748; 977/82; 977/845

(58) Field of Classification Search ............. 209/2, 4, 209/162, 172, 233; 423/445 R, 445 B, 461; 977/745, 748, 842, 845
    See application file for complete search history.

(56) References Cited

U.S. PATENT DOCUMENTS

| | | | | |
|---|---|---|---|---|
| 5,711,927 | A * | 1/1998 | Atwood et al. | 423/445 B |
| 7,029,645 | B2 * | 4/2006 | Burgin | 423/447.1 |
| 7,131,537 | B2 * | 11/2006 | Papadimitrakopoulos | 209/18 |
| 7,938,987 | B2 * | 5/2011 | Grigorian et al. | 252/502 |
| 7,939,047 | B2 * | 5/2011 | Tour et al. | 423/460 |

FOREIGN PATENT DOCUMENTS

JP        11-240705 A  *  9/1999

* cited by examiner

Primary Examiner — Thomas M Lithgow
(74) Attorney, Agent, or Firm — Nixon Peabody LLP (57) ABSTRACT

A method of separating at least one carbon nanotube having a desired diameter and/or chirality from a mixture of carbon nanotubes having different diameters and/or chiralities is provided. A calixarene of formula (I):

(I)

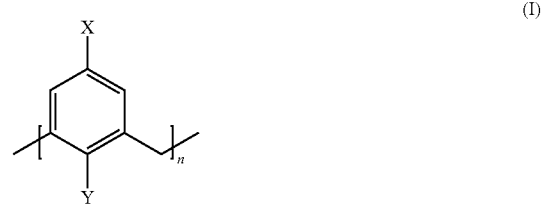

wherein $n \geq 4$; X is $PO_3H_2$, $R_a$—$PO_3H$, $SO_3H$, or $R_a$—$SO_3H$; Y is $R_b$, OH, or $OR_b$; and $R_a$ and $R_b$ are independently selected from the group consisting of optionally substituted alkyl, optionally substituted aryl, optionally substituted arylene alkyl and optionally substituted alkylene aryl is combined with the mixture of carbon nanotubes in an aqueous solvent to produce an aqueous supernatant containing the carbon nanotube(s) having the desired diameter and/or chirality. The aqueous supernatant containing the carbon nanotube(s) is then separated from a residue comprising the remaining carbon nanotubes of the mixture. Semi-conducting or metallic carbon nanotubes may also be separated from a mixture of carbon nanotubes by combining a calixarene of formula (I) with the mixture of carbon nanotubes in an aqueous solvent and separating an aqueous supernatant containing either the metallic or semi-conducting carbon nanotubes from a residue comprising the remaining carbon nanotubes of the mixture.

13 Claims, 9 Drawing Sheets

METHODS FOR SELECTIVELY SEPARATING CARBON NANOTUBES

CROSS REFERENCE TO RELATED APPLICATIONS OR PRIORITY CLAIM

This application claims priority of Australian Patent Application No. 2008906319, filed Dec. 5, 2008 and Australian Patent Application No. 2008905620, filed Oct. 31, 2008.

DESCRIPTION

1. Field

The present invention relates to novel complexes of functionalized calixarenes and carbon nanotubes, in particular to complexes of functionalized calixarenes and carbon nanotubes that are readily soluble in aqueous media. Consequently, the present invention also relates to methods for dispersing carbon nanotubes in aqueous media and facilitating purification and processing thereof. Additionally, the present invention relates to methods for selectively separating carbon nanotubes on the basis of their diameter, chirality, and electronic properties.

2. Background

Since the discovery of carbon nanotubes (CNTs) by Iijima and more recently single-walled carbon nanotubes (SWCNTs), these purely carbon-based materials have attracted significant attention from both the research and commercial sectors. CNTs have extraordinary mechanical and unique electrical properties with major research efforts focused on areas such as high performance electronics, scanning probe microscopy, fuel cells, composites, chemical, biological and physical sensors, and many more. In order to harness the full potential of CNTs, the ability to separate them according to diameter and/or chirality is required. The diameter and inherent chirality of SWCNTs directly controls their semiconducting or metallic properties.

Recent methods have been trialed to separate CNTs including pioneering work by Bao, et al. which utilises different absorption properties of metallic and semiconducting SWNTs towards amine- and phenyl-terminated silanes to produce a one-step methodology for self-sorting and aligned thin-film transistors. Other methods include dielectrophoresis which take advantage of the difference in relative dielectric constants of metallic and semiconducting CNTs in respect to the choice of solvent. Pathways utilizing differential density gradient systems have also been explored. More recent research has targeted non-covalent supramolecular interactions, as in biopolymers, DNA-wrapping, porphyrinic polypeptides and oligo-acene adducts. The problem with some of these methods is that the supramolecular chemistry is carried out in organic solvents with limited stability in aqueous media, and require lengthy experimental procedures. Progress has been made to combat these underlying problems with the use of amphiphilic polymers. Supramolecular systems that can be utilized to solubilize SWCNTs in aqueous media, are potentially more benign, generating less waste, and are thus more attractive.

The present invention seeks to overcome at least some of the above mentioned disadvantages.

SUMMARY

The present invention provides a method for separating carbon nanotubes of a desired diameter and/or chirality, or separating semiconducting and metallic carbon nanotubes from a mixture of carbon nanotubes. The present invention also provides some novel complexes of calixarenes and carbon nanotubes, a process of producing the complexes, a method for dispersing carbon nanotubes in an aqueous solvent and method facilitating purification and processing thereof.

Accordingly, in a first aspect, the invention provides a method of separating at least one carbon nanotube having a desired diameter and/or chirality from a mixture of carbon nanotubes having different diameters and/or chiralities comprising:

(a) selecting a calixarene of formula (I):

(I)

wherein $n \geq 4$; X is $PO_3H_2$, $R_a$—$PO_3H$, $SO_3H$, or $R_a$—$SO_3H$; Y is $R_b$, OH, or $OR_b$; and $R_a$ and $R_b$ are independently selected from the group consisting of optionally substituted alkyl, optionally substituted aryl, optionally substituted arylene alkyl and optionally substituted alkylene aryl;

(b) combining the mixture of carbon nanotubes with the selected calixarene of step (a), in an aqueous solvent, to produce an aqueous supernatant containing the carbon nanotube(s) having the desired diameter and/or chirality; and (c) separating the aqueous supernatant of step (b) containing the carbon nanotube(s), from a residue comprising the remaining carbon nanotubes of the mixture.

The term "carbon nanotube mixture" as used herein should be understood to refer to structurally and/or characteristically heterogeneous CNTs or SWCNTs, and may also refer to loose or bulk carbon nanotubes produced from any of the current or future techniques of CNT production described above. Carbon nanotube material is structurally heterogeneous in that the length and diameter of each CNT will vary within the carbon nanotube material. Typically, the size distribution relating to the diameter of the carbon nanotube material may vary in the range of 0.5 nm to 20 nm, with certain diameters being more prevalent within a sample of carbon nanotube material than others, the size distribution and predominant diameters often depending on the production technique used to fabricate the carbon nanotube material.

In one embodiment, the calixarene of formula (I) and the carbon nanotube(s) contained in the aqueous supernatant form a complex.

In another embodiment, the carbon nanotube(s) that are contained in the aqueous supernatant are isolated by evaporation of the aqueous solvent.

In a further embodiment, the carbon nanotube(s) contained in the residue are isolated by decanting off the aqueous solvent or filtering out the residue.

The invention further provides a method of separating at least one semiconducting carbon nanotube or at least one metallic carbon nanotube from a mixture of carbon nanotubes comprising:

(a) selecting a calixarene of formula (I) as defined above;

(b) combining the mixture of carbon nanotubes, in an aqueous solvent, to produce an aqueous supernatant containing either the metallic carbon nanotube(s) or semi-conducting carbon nanotube(s); and (c) separating the aqueous supernatant of step (b) containing either the metallic carbon nanotube(s) or semi-conducting carbon nanotube(s), from a residue comprising the remaining nanotubes of the mixture.

By this method, one of the semiconducting carbon nanotubes and metallic carbon nanotubes will be dispersed in the aqueous supernatant, with the remainder of the mixture of nanotubes remaining as a residue. The metallic or semi-conducting carbon nanotubes contained in the aqueous supernatant may then be isolated by evaporation of the aqueous solvent. This method also allows the metallic or semi-conducting carbon nanotubes contained in the residue to be isolated. The residue may be isolated by decanting off the aqueous solvent or by filtering out the residue.

In one embodiment, the calixarene of formula (I), and either the metallic carbon nanotube(s) or the semi-conducting carbon nanotube(s), contained in the aqueous supernatant form a complex.

In another embodiment, either the metallic carbon nanotube(s) or the semi-conducting carbon nanotube(s) that are contained in the aqueous supernatant are isolated by evaporation of the aqueous solvent.

In a further embodiment, the carbon nanotube(s) contained in the residue are isolated by decanting off the aqueous solvent or filtering out the residue.

In a second aspect, the present invention provides novel complexes of functionalized calixarenes and carbon nanotubes. Accordingly, the present invention provides a complex comprising at least one carbon nanotube and at least one calixarene of formula (I) as described above, provided that:

(i) when X is $PO_3H_2$; Y is not OH; or
(ii) when X is $SO_3H$; Y is not OH or $OR_b$; wherein $R_b$ is as defined above.

In another embodiment of the invention, the complex comprises at least one carbon nanotube and at least one calixarene of formula (I) as defined above, wherein X is $R_a$—$PO_3H$ or $R_a$—$SO_3H$; Y is $R_b$, OH, or $OR_b$; and n, $R_a$ and $R_b$ are as defined above.

In a further embodiment of the invention, the complex comprises at least one carbon nanotube and at least one calixarene of formula (I) as defined above, wherein X is $PO_3H_2$; Y is $OR_b$; and n and $R_b$ are as defined above.

In a still further embodiment of the invention, the complex comprises at least one carbon nanotube and at least one calixarene of formula (I) as defined above, wherein X is $SO_3H$; Y is $R_b$; and n and $R_b$ are as defined above.

The complex defined above may have the at least one calixarene bound at the surface of a single carbon nanotube.

The carbon nanotube of the invention may be any known types of carbon nanotubes. For example, the nanotubes may be single-walled nanotubes (SWNTs), double walled carbon nanotubes (DWNTs) and/or multi-walled nanotubes (MWNTs). In a preferred embodiment of the invention, the carbon nanotubes are single-walled carbon nanotubes.

In a third aspect, the present invention provides method of preparing a complex, which comprises combining, in an aqueous solvent, at least one carbon nanotube and at least one calixarene as defined in above, to produce an aqueous supernatant containing the complex of the carbon nanotube and the calixarene.

In a fourth aspect, the present invention provides a method of preparing a mono-dispersion of carbon nanotubes comprising the step of combining, in an aqueous solvent, a carbon nanotube or a mixture of carbon nanotubes with at least one calixarene as defined above, wherein the calixarene forms a complex with the carbon nanotube, and is mono-dispersed in the aqueous solvent.

The method may further comprise the additional step of evaporating the aqueous solvent of the aqueous supernatant to leave the complex of the carbon nanotube and the calixarene. Where the aqueous supernatant also includes a residue comprising any remaining carbon nanotubes, the residue may optionally be separated from the supernatant.

In a fifth aspect, the present invention provides a method of preparing a mono-dispersion of a complex comprising the step of combining, in an aqueous solvent, a mixture of carbon nanotubes with at least one calixarene as defined above, wherein the calixarene forms a complex with the carbon nanotube(s), and is mono-dispersed in the aqueous solvent.

In a sixth aspect, the present invention provides a method of separating impurities from a mixture of carbon nanotubes comprising the steps of:

(a) combining in an aqueous solvent, the mixture of carbon nanotubes with at least one calixarene as defined above, to produce an aqueous supernatant containing the nanotubes and a residue comprising the impurities; and (b) separating the aqueous supernatant of step (a) from the residue containing the impurities of the mixture.

The impurities from a mixture of carbon nanotubes may arise from the production of carbon nanotube material by any of the current or future techniques of carbon nanotube production. Impurities present in carbon nanotube mixture are not limited to a carbon nanotube material solely containing contaminants arising from the production technique used to produce the carbon nanotube material.

Impurities include but are not limited to amorphous carbon and metal catalysts.

In one embodiment, the nanotubes contained in the aqueous supernatant may be present as a complex with at least one calixarene.

DESCRIPTION OF THE FIGURES ACCOMPANYING THE DESCRIPTION

The invention is described further by way of example with reference to the accompanying drawings in which.

DETAILED DESCRIPTION

The present invention provides a method of separating a carbon nanotube having a desired diameter and/or chirality from a mixture of carbon nanotubes having different diameters and/or chiralities. The invention also relates to novel complexes of carbon nanotubes, and methods which involve the novel complexes.

Nanotubes are typically small cylinders made of organic or inorganic materials. Known types of nanotubes include carbon nanotubes, inorganic nanotubes and peptidyl nanotubes. Inorganic nanotubes include $WS_2$ and metal oxide nanotubes such as oxides of titanium and molybdenum. The nanotubes of the present invention are carbon nanotubes (CNTs).

CNTs are sheets of graphite that have been rolled up into cylindrical tubes. The basic repeating unit of the graphite sheet consists of hexagonal rings of carbon atoms, with a carbon-carbon bond length of about 1.45 Å. Depending on how they are made, the nanotubes may be single-walled nanotubes (SWNTs), double walled carbon nanotubes (DWNTs) and/or multi-walled nanotubes (MWNTs). A typical SWNT has a diameter of about 0.7 to 1.4 nm. In a preferred embodiment of the present invention the carbon nanotubes are single-walled nanotubes.

The structural characteristics of nanotubes provide them with unique physical properties. Nanotubes may have up to 100 times the mechanical strength of steel and can be up to several mm in length. They exhibit the electrical characteristics of either metals or semiconductors, depending on the degree of chirality or twist of the nanotube. Different forms of nanotubes are known as armchair, zigzag and chiral nanotubes. The electronic properties of carbon nanotubes are determined in part by the diameter and therefore the 'form' of the nanotube.

As used herein, the terms "carbon nanotubes", "single-walled carbon nanotubes", or "SWCNT" should be understood to include carbon nanotubes or single-walled carbon nanotubes, respectively, synthesized by any current or future techniques and having any physical properties (eg. electronic type or chirality) or dimensions (eg. individual diameter or length) achieved by such current or future techniques unless otherwise stated or inferred from the description. Illustrative examples of current techniques for producing CNTs and SWCNTs include high pressure carbon monoxide decomposition, Co—Mo catalysis, laser ablation, arc discharge, and chemical vapour deposition.

The term "carbon nanotube mixture" as used herein should be understood to refer to structurally and/or characteristically heterogeneous CNTs or SWCNTs, and may also refer to loose or bulk carbon nanotubes produced from any of the current or future techniques of CNT production described above. Loose or bulk carbon nanotubes are distinguished from carbon nanotubes that are grown on and adhered to a substrate for a particular end use thereon. Further, it will be appreciated that a carbon nanotube mixture substantially comprises "bundles" of CNTs or SWCNTs comprising a plurality of discrete CNTs or SWCNTs bound together by van der Waals forces and other secondary bonding interactions, and that a reference to loose or bulk does not refer to a plurality of discrete CNTs or SWCNTs, but rather to a plurality of bundles of heterogeneous CNTs or SWCNTs.

Typically, an as-received carbon nanotube material produced from any of the current or future techniques of CNT production described above may contain impurities arising from the production technique, including but not limited to amorphous carbon and metal catalysts. However, it should be understood that a reference herein to "impurities" present in carbon nanotube mixture are not limited to a carbon nanotube material solely containing contaminants arising from the production technique used to produce the carbon nanotube material.

Carbon nanotube material is structurally heterogeneous in that the length and diameter of each CNT will vary within the carbon nanotube material. Typically, the size distribution relating to the diameter of the carbon nanotube material may vary in the range of 0.5 nm to 20 nm, with certain diameters being more prevalent within a sample of carbon nanotube material than others, the size distribution and predominant diameters often depending on the production technique used to fabricate the carbon nanotube material.

Calixarenes are cyclic phenolic oligomers wherein two adjacent phenol rings are linked together by an ortho-ortho methylene bridge. These phenolic oligomers may be tetramers, hexamers and octamers are well known, as are several calixarenes having an odd number of rings in their molecule. The lowest oligomer in the series of calix[n]arene derivatives has four phenol moieties (i.e. calix[4]arene). Calixarenes having less than four phenolic rings are not available The p-substituted calix[4]arene may assume a bowl shape conformation, while higher calixarenes are more flexible and may not necessarily take on a cone or bowl shape conformation.

The term "alkyl" refers to optionally substituted straight chain and optionally substituted branched chain alkyl groups generally of from 1 to about 20 carbon atoms in length. Examples of alkyl groups include methyl, ethyl, propyl, isopropyl, butyl, isobutyl, sec-butyl, tert-butyl, pentyl, neopentyl, hexyl and the like.

The term "aryl" refers to optionally substituted single polynuclear, conjugated or fused residues of aromatic hydrocarbons. Examples of aryl groups include phenyl, biphenyl, terphenyl, quaterphenyl, napthyl, tetrahydronapthyl, anthracenyl, dihydroanthracenyl, benzanthracenyl, dibenzanthracenyl and phenanthrenyl. In a preferred embodiment, aryl is selected from phenyl and naphthyl.

The term "arylene alkyl" is taken to refer to the divalent version of the aryl groups as defined above, which are substituted by one or more alkyl group(s). The alkyl groups are as defined above. In a preferred embodiment, arylene alkyl is selected a phenyl or naphthyl groups that is substituted by one or more $C_1$-$C_{20}$alkyl, hydroxy, or $C_1$-$C_{20}$alkoxy.

The term "alkylene aryl" is taken to refer to a divalent version of the alkyl groups as defined above, which are substituted by one or more aryl group(s). The aryl groups are as defined above.

The term "substituted" refers to a group that may or may not be further substituted with one or more groups selected from $C_{1-6}$alkyl, $Si(C_{1-6}alkyl)3$, $C_{3-6}$cycloalkyl, $C_{2-6}$alkenyl, $C_{2-6}$alkynyl, aryl, heterocycylyl, halo, halo$C_{1-6}$alkyl, halo $C_{3-6}$cycloalkyl, halo$C_{2-6}$alkenyl, halo$C_{2-6}$alkynyl, haloaryl, haloheterocycylyl, hydroxy, $C_{1-6}$alkoxy, $C_{2-6}$alkenyloxy, $C_{2-6}$alkynyloxy, aryloxy, heterocyclyloxy, carboxy, halo$C_{1-6}$ alkoxy, halo$C_{2-6}$alkenyloxy, halo$C_{2-6}$alkynyloxy, haloaryloxy, nitro, nitro$C_{1-6}$alkyl, nitro$C_{2-6}$alkenyl, nitroaryl, nitroheterocyclyl, azido, amino, $C_{1-6}$alkylamino, $C_{2-6}$alkenylamino, $C_{2-6}$alkynylamino, arylamino, heterocyclamino acyl, $C_{1-6}$alkylacyl, $C_{2-6}$alkenylacyl, $C_{2-6}$alkynylacyl, arylacyl, heterocycylylacyl, acylamino, acyloxy, aldehydo, $C_{1-6}$alkylsulfonyl, arylsulfonyl, $C_{1-6}$alkylsulfonylamino, arylsulphonylamino, $C_{1-6}$alkylsulfonyloxy, arylsulfonyloxy, $C_{1-6}$alkylsulfenyl, $C_{2-6}$alklysulfenyl, arylsulfenyl, carboalkoxy, carboaryloxy, mercapto, $C_{1-6}$alkylthio, arylthio, acylthio, cyano and the like.

The calixarenes of the invention may also be prepared as salts. Examples of salts include alkaline earth metal salts; sodium, potassium, lithium, ammonium and alkylammonium salts; and acid addition salts of inorganic acids such as hydrochloric, orthophosphoric, sulfuric, phosphoric, nitric, carbonic, boric, sulfamic and hydrobromic acids.

The calixarenes of formula (I) behave in aqueous media as surfactant molecules. The phosphonated calixarenes of formula (I) are amphiphilic compounds in that they contain both hydrophobic groups (the ring of linked para-substituted benzene moieties) and hydrophilic groups (the substituents located at the rim of the calixarene).

The inventors of the present invention have found that the calixarenes of formula (I) of the present invention selectively bind to particular diameter CNTs, which is highly dependent on the nature of the calixarene selected for complexation. Interestingly, the diameter for which the calixarene of formula (I) is selective is not necessarily the most abundant in the as-received carbon nanotube material.

Generally, smaller diameter CNTS are more readily solubilised into aqueous media by complexation with calixarenes of formula (I). However, CNTs with larger diameters can be solubilised when using calixarenes of formula (I) where n is 7 or 8, which is consistent with the increased conformational flexibility of the larger ring size calixarenes of formula (I). In one form of the invention the calixarenes of formula (I) are selective for CNTs having diameters in the range 0.89 nm-1.35 nm, preferably in the range of 0.89 nm-1.04 nm.

It will be appreciated that the calixarenes of formula (I) of the present invention may be selective for CNTs having one or more diameters in the range 0.89 nm-1.35 nm.

Structural heterogeneity of carbon nanotube material also resides in the chiralities or chiral angles displayed by the CNTs. The inventors of the present invention have realised that the calixarenes of formula (I) of the present invention selectively bind to CNTs having a particular chiral angle or chirality. Again, the selectivity displayed by the calixarenes of the present invention is highly dependent on the nature of the calixarene selected for complexation.

It will be appreciated that the calixarenes of formula (I) of the present invention may be selective for CNTs having one or more chiralities or chiral angles.

In another aspect of the invention, one may separate carbon nanotubes having a desired diameter and/or chirality from a carbon nanotube material by reacting the carbon nanotube material with a calixarene of formula (I) as defined herein in aqueous media, wherein said calixarene is selected to selectively bind to carbon nanotubes having the desired diameter and/or chirality, and producing an aqueous supernatant containing a mono-dispersion of carbon nanotubes having the desired diameter and/or chirality, and a remaining residue; and then separating the aqueous supernatant from the residue. Appropriate separation techniques will be well known to the person skilled in the art.

It will be appreciated that the aqueous supernatant will contain those CNTs for which the selective calixarene of formula (I) shows binding affinity. It will also be appreciated that the remaining residue will contain those CNTs for which the selective calixarene of formula (I) does not show binding affinity and consequently were not solubilised in aqueous media.

Advantageously, the calixarenes of formulae (I) preferentially bind to carbon nanotubes in comparison to amorphous carbon and metal catalyst particles in contaminated carbon nanotube material, such as, for example, unpurified carbon nanotube material produced following carbon nanotube production methods.

The method of separating a carbon nanotube of desired diameter and/or chirality from a mixture of carbon nanotubes involves the step of combining the mixture of carbon nanotubes with the selected calixarene, in an aqueous solvent.

The carbon nanotubes and the calixarenes are combined by any suitable known technique to mix the components, such as, for example, ultrasonification.

The term "aqueous solvent" is taken to refer to a solvent that includes water and may also include water-miscible solvents, salts, acids, bases, buffers, or other additives that may dissolve in water. For example the aqueous solvent comprising water may also include ethanol, sodium chloride, sodium hydroxide, hydrochloric acid, sulfuric acid and the like. In a preferred embodiment the aqueous solvent is water.

The calixarenes of formula (I) of the present invention will selectively bind to CNTs of particular diameter and/or chirality that are present in the mixture of carbon nanotubes in aqueous solvent. The calixarenes of formula (I) bound to the particular CNTs will be present in, the aqueous supernatant and can be separated from the rest of the mixture of CNTs which are present as a residue.

The residue may contain the carbon nanotubes of the mixture that are not separated into the aqueous supernatant. The residue may also contain impurities arising from the production technique, including but not limited to amorphous carbon and metal catalysts.

Separation of the aqueous supernatant from the residue may be performed by any known suitable technique, such as, for example, filtration and/or centrifugation.

Generally the electronic nature of a CNT is dependent on the diameter and chirality of the CNT. Approximately about two thirds of CNTs in a carbon nanotube material are semiconducting. The calixarenes of formula (I) of the present invention may selectively bind to semi-conducting CNTs or metallic CNTs. The selectivity displayed by the calixarenes of the present invention for metallic or semi-conducting CNTs is highly dependent on the nature of the calixarene selected for complexation with the CNTs. It will be appreciated that the calixarenes of formula (I) of the present invention may be selective for one or more semi-conducting CNTs having one or more diameters and/or chiralities, or the calixarenes of formula (I) of the present invention may be selective for one or more metallic CNTs having one or more diameters and/or chiralities.

This selectivity is used in the method to separate semiconducting carbon nanotubes or metallic carbon nanotubes from a mixture of carbon nanotubes. The method Again, it will be appreciated that the aqueous supernatant will contain those CNTs for which the selective calixarene of formula (I) shows binding affinity, while the remaining residue will contain those CNTs for which the selective calixarene of formula (I) does not show binding affinity and consequently were not solubilised in aqueous media.

The metallic or semi-conducting carbon nanotubes contained in the aqueous supernatant may then be isolated by drying the aqueous supernatant. Conversely, the metallic or semi-conducting carbon nanotubes contained in the residue may then be isolated according to practices well understood in the art.

In one embodiment, when the calixarenes of the invention are combined with the carbon nanotubes, they may form a complex. Accordingly, the present invention also provides some novel complexes of functionalized calixarenes and carbon nanotubes. The complexes of carbon nanotubes and calixarenes include calixarenes of formula (I):

(II)

wherein $n \geq 4$; X is $PO_3H_2$, $R_a$—$PO_3H$, $SO_3H$, or $R_a$—$SO_3H$; Y is $R_b$, OH, or $OR_b$, and $R_a$ and $R_b$ are independently selected from the group consisting of optionally substituted alkyl, optionally substituted aryl, optionally substituted arylene alkyl and optionally substituted alkylene aryl, provided that:

(i) when X is PO$_3$H$_2$, Y is not OH; or
(ii) when X is SO$_3$H, Y is not OH or OR$_b$, wherein R$_b$ is as defined above.

These complexes of carbon nanotubes and calixarenes of formula (I) are formed via a variety of bonding interactions. These bonding interactions may include covalent bonds, ionic bonds, co-ordinate bonds and non-covalent bonding interactions. The non-covalent bonding interactions may include hydrogen bonding, ionic interactions, Van der Waals interactions, dispersion forces and hydrophobic interactions. The non-covalent bonding network may also include non-covalent bonds mediated by solvent molecules. The complex of carbon nanotubes and calixarenes of formula (I) may self-assemble, which is facilitated by the conformational flexibility and functionality of the calixarenes of formula (I). This conformational flexibility and functionality allows shape complementarity between the calixarenes and the surface of individual carbon nanotubes, and assists the formation of bonding interactions to form calixarene-carbon nanotube complexes.

The complexes of the present invention which comprise carbon nanotubes and at least one calixarene of formula (I) as defined above, can be readily prepared. The complex is prepared by combining, in an aqueous solvent, the carbon nanotubes and at least one calixarene, to produce an aqueous supernatant containing the carbon nanotubes.

In a preferred embodiment, the aqueous solution of the calixarene of formula (I) is mixed with an aqueous dispersion of carbon nanotubes in the form of an as-received carbon nanomaterial in water. The carbon nanotubes and the calixarene may be mixed under ambient conditions for a period of between about 5 minutes to about 60 minutes, preferably for a period of between about 10 minutes to about 30 minutes, to afford black to light grey solutions (FIG. 1) thereby indicating the ready solubilisation of the complexes of the present invention into aqueous media. The carbon nanotubes and the calixarenes are combined by any known technique to mix the components, including using ultrasonification.

The aqueous supernatant may simply be evaporated at this stage. Alternatively, if a residue is present, then the residue can be separated from a residue which may contain any of the impurities of the mixture.

To facilitate removal of solid impurities and large agglomerations suspended in the aqueous media, the mixture may be centrifuged and the resultant supernatant solutions containing the complexes of the present invention may be collected. The intense colouration maintained in the aqueous supernatant after centrifugation is stable for over six months, indicating that the calixarenes of formula (I) are highly effective in solubilising and stabilizing carbon nanotubes in aqueous media.

The complexes may be recovered as solid residues by drying the supernatant solutions. Each of FIGS. 2-6 demonstrate that the carbon nanotubes are observed to be discrete carbon nanotubes rather than "bundles" of carbon nanotubes, indicating the disruption of van der Waals forces between CNT bundles and subsequent self assembly of the calixarene around a surface of a discrete CNT for effective solubilisation thereof into aqueous media. Accordingly, the complexation of calixarenes of formula (I) with CNTs in aqueous media affords a mono-dispersion of carbon nanotubes in aqueous media. In this method, the mono-dispersion of carbon nanotubes will be prepared by combining, in an aqueous solvent, the carbon nanotubes and at least one calixarene of formula (I).

It will be appreciated that he mono-dispersion may also be a nano-dispersion of carbon nanotubes in an aqueous solvent.

Advantageously, the calixarenes of formula (I) also preferentially bind to carbon nanotubes in comparison to amorphous carbon and metal catalyst particles in contaminated carbon nanotube material, such as, for example, unpurified carbon nanotube material produced following carbon nanotube production methods. The calixarenes of formula (I) of the present invention, therefore, have a low binding affinity to amorphous carbon and other contaminants such as metal catalysts. Accordingly, one may also remove impurities from the carbon nanotube material by combining a carbon nanotube mixture with a calixarene of formula (I) in aqueous media to produce an aqueous supernatant containing a mono-dispersion of carbon nanotubes. The impurities from the carbon nanotube material will form a residue, and may be separated from the aqueous supernatant.

The method of separating the impurities from a mixture of carbon nanotubes involves combining the mixture of carbon nanotubes and impurities with at least one calixarene, to produce an aqueous supernatant containing the carbon nanotubes. This step is followed by the separation of the aqueous supernatant from a residue containing the impurities of the mixture.

It will be appreciated that the residue contains the contaminants residing in the contaminated carbon nanotube material. In one form of the invention the aqueous supernatant may be readily separated from the residue by centrifuging the mixture and collecting the aqueous supernatant containing the mono-dispersion of carbon nanotubes. Appropriate separation techniques will be well known to the person skilled in the art.

This aspect of the present invention may be applied in post-growth purification protocols in conjunction with any one of the current or future techniques used to produce CNTs or SWCNTs.

The invention will be illustrated in greater detail with reference to the following non-limiting examples.

EXAMPLE 1

Materials and Methods

SWCNTs (Elicarb®) were purchased from Thomas Swan & Co. (UK) which were produced by a catalytic chemical vapour deposition synthesis method with an as-received purity>90% (4.79 wt % ash, 2.76 wt % iron catalyst, <2 nm tube diameter). The calixarenes referred to in the examples study are detailed in Table 1. They include p-phosphonic acid calix[n]arenes (n=4, 6, 8), 1A, 2A, and 3A, p-phosphonic acid calix[4]arene modified by octadecyl and butyl substituents on the lower rim, 1B and 1C, p-phosphonic acid calix[6]arene modified by methyl substituents on the lower rim, 2B, p-sulfonato-calix[8]arene, 4A, p-benzyl-sulfonato-calix[8]arene, 4B, and p-phenyl-sulfonato-calix[8]arene, 4C.

TABLE 1

Notation for calix[n]arene systems.

| Notation | X | Y | n |
|---|---|---|---|
| 1A | PO$_3$H$_2$ | OH | 4 |
| 1B | PO$_3$H$_2$ | C$_{18}$H$_{37}$ | 4 |
| 1C | PO$_3$H$_2$ | OBu | 4 |

TABLE 1-continued

Notation for calix[n]arene systems.

| Notation | X | Y | n |
|---|---|---|---|
| 2A | PO$_3$H$_2$ | OH | 6 |
| 2B | PO$_3$H$_2$ | OMe | 6 |
| 3A | PO$_3$H$_2$ | OH | 8 |
| 4A | SO$_3$H | OH | 8 |
| 4B | Benzyl-SO$_3$H | OH | 8 |
| 4C | Phenyl-SO$_3$H | OH | 8 |

Compounds 1A-3A were prepared as described in T. E. Clark, M. Makha, A. N. Sobolev, H. Rohrs, J. L. Atwood and C. L. Raston, Chem. Eur. J., 2008, 14, 3931-3938 and S. Shinkai, S. Mori, H. Koreishi, T. Tsubaki and O. Manabe, J. Am. Chem. Soc., 1986, 108, 2409-2416; which are incorporated herein by reference. The p-sulfonato-calixarene (4A) was synthesized via a modified preparation, as described in S. Shinkai, S. Mori, H. Koreishi, T. Tsubaki and O. Manabe, J. Am. Chem. Soc., 1986, 108, 2409-2416 with the 'extended arm' p-sulfonato-calixarenes (4B & 4C) synthesized as described in M. Makha and C. L. Raston, Tetrahedron Lett., 2001, 42, 6215-6217, and M. Makha and C. L. Raston, Chem. Commun., 2001, 23, 2470-2471, which are incorporated herein by reference.

Figure 1:
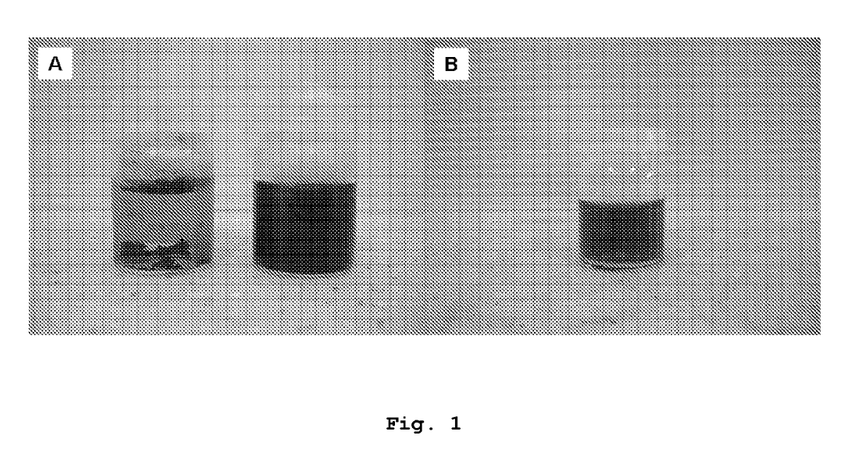
FIG. 1 are photographs of solutions of carbon nanotubes solubilised in accordance with the present invention.

A typical experiment consists of the addition of as-received SWCNTs (1.0 mg) into a sample vial (10 mL) containing Milli-Q water (6 mL, 18 MΩ cm$^{-1}$). To this mixture the appropriate calixarene (2.60×10$^{-2}$ mmol) was added. This mixture was ultrasonicated for 10 minutes with a sonic lance (4 W RMS power, Branson Sonifier 150) and a further 30 minutes (5 W RMS power), affording black to light grey solutions (FIG. 1A). To remove impurities and large agglomerations the solution was divided into 1.5 mL aliquots and centrifuged (5000RCF, Eppendorf Mini Spin plus) for 30 minutes in ambient conditions. The top three quarters of the supernatant was collected and combined, yielding the solubilized product (FIG. 1B).

Raman spectroscopy was performed using a Raman Systems, R-3000CN portable Raman spectrometer. The spectral range covered was 100 to 1800 cm$^{-1}$, with an excitation wavelength of 785 nm, and laser power<10 mW. Spectra were acquired from multiple areas and rotations; the samples were prepared by drop-coating the resulting supernatants onto aluminum foil and allowed to air dry. Raman spectra of calixarene control samples were also prepared and collected using this methodology. UV-visible spectrophotometry was performed with a Varian, Cary 50 Tablet spectrophotometer. The spectral range covered was 800 to 200 nm, with a scan rate of 600 nm/min; the samples were prepared by dilution (100×) of the resulting supernatants, and were analysed in quartz cuvettes with a 10 mm path length. Transmission electron microscopy (TEM) was performed on a JEOL 2100 TEM operating at 120 kV; sample preparation involved centrifugation of the supernatant (100× dilution) and re-dispersing the resultant plug in Milli-Q water, from which a drop of the solution was placed onto a holey carbon film supported by copper grids and air-dried.

Results and Discussion

All the calixarenes studied are essentially acting as surfactant molecules, in solubilizing the SWCNTs. It is interesting to note that during ultrasonication all the solutions containing the calixarenes formed a black solution (FIG. 1A), with exception of 1A & 1B which afforded light grey suspensions. In comparison, the SWCNT/water experiment devoid of calixarenes formed large aggregates of the SWCNT material (FIG. 1A). The transformation from colourless to black and/or grey indicates the effective solubilization of the SWCNT material into the aqueous media. This is further supported with the intense colouration maintained in the supernatant after centrifugation (FIG. 1B). It should be noted that the collected supernatant suspensions of 1A-4C are highly homogeneous and are stable for over six months, and thus the p-phosphonated calixarenes and 'extended arm' p-sulfonated calixarenes are effective in solubilizing and stabilizing SWCNTs in aqueous media.

Raman Spectroscopy

To obtain a greater understanding of the material solubilized by the calixarene systems, the supernatant solutions were dried and the resulting residues were analyzed using Raman spectroscopy. Raman scattering produces characteristic peaks from certain phonon modes in carbon nanotubes. The frequencies of immediate interest revolve around the radial breathing modes (RBMs) and the G- & D-bands. The low frequency RBMs (100-300 cm$^{-1}$) are directly dependant on the nanotube diameters within a sample. The high-frequency band at ~1340 cm$^{-1}$ is commonly referred to as the D-band (Disorder-induced band) and provides information regarding amorphous impurities and carbon nanotube wall disorder. The high-frequency band at ~1585 cm$^{-1}$ is commonly referred to as the G-band (Graphite band) and relates to the graphite E$_{2g}$ symmetry of the interlayer mode. This mode represents the structural intensity of the sp$^2$-hybridized carbon atoms of the CNTs and is sensitive to the nanotube surroundings. It is common to utilise the calculated I$_D$/I$_G$ ratio to assess the quality of a CNT sample following a purification procedure. It should be noted that Raman spectra were obtained for all calixarene control samples, and were found to not be Raman active at the laser frequency utilised in this study.

TABLE 2

Raman spectral G-band frequency shifts and the I$_D$/I$_G$ ratios for the residues of the calixarene/SWCNT supernatants.

| Sample | G-band frequency (cm$^{-1}$) | Frequency shift (cm$^{-1}$) | I$_D$/I$_G$ ratio |
|---|---|---|---|
| As-received SWCNTs | 1583.68 | — | 0.2131 |
| 1A | 1592.48 | +8.80 | 0.1613 |
| 1B | 1588.08 | +4.40 | 0.1816 |
| 1C | 1588.96 | +5.28 | 0.0729 |
| 2A | 1592.48 | +8.80 | 0.1559 |
| 2B | 1594.24 | +10.56 | 0.1350 |
| 3A | 1592.48 | +8.80 | 0.2449 |
| 4A | 1592.48 | +8.80 | 0.1277 |
| 4B | 1602.15 | +18.47 | 0.2514 |
| 4C | 1602.15 | +18.47 | 0.1440 |

The spectral shifts in the calixarene/SWCNT systems are detailed in relation to the as-received SWCNT sample (Table 2). All of the calixarene systems produce an up-field shift in the G-band frequency (Table 2), shown in FIGS. 3A & 4A. For the p-phosphonated calixarene analogues the largest shift was seen for 2B, with the least shift seen for 1B. For the latter, this may be related to the large hydrophobic tail decreasing its solubility in aqueous media. The hierarchy of frequency shift is 1B<1C<1A, 2A, 3A<2B (Table 2), and this gives some insight into the relative strength of the interaction between the respective p-phosphonated calixarene and the SWCNTs. The results show that the interplay between the calixarenes and SWCNTs leads to their solubilization into the aqueous media.

Figure 4A:
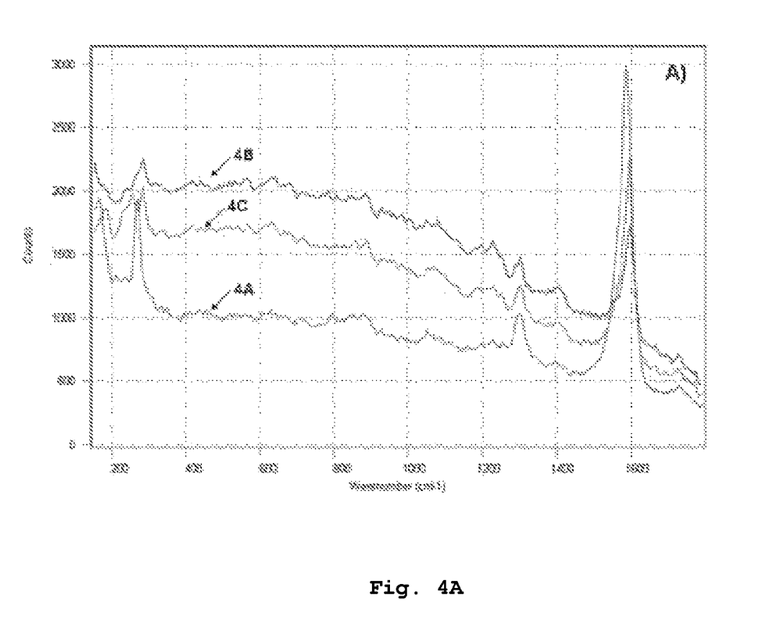
FIGS. 4A and 4B show Raman spectra of further calixarene-carbon nanotube complexes prepared in accordance with the present invention.
Figure 4B:
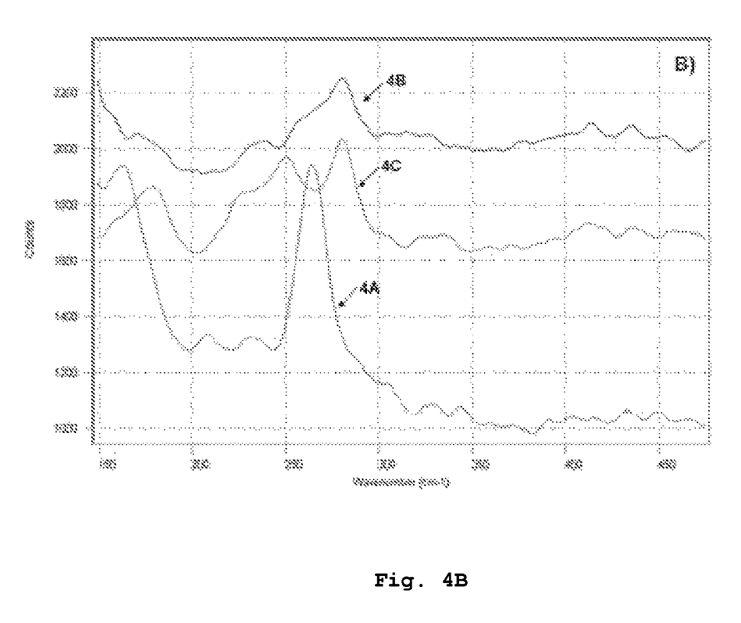

Similarly, with the p-sulfonated calixarene systems significant G-band shifts were observed with the largest up-field shifts attributed to the 'extended arm' p-sulfonated calix[8]arene systems (4B & 4C) (FIG. 4A). This could be due to more efficient packing of the calixarenes around the SWCNT surface. The conformational flexibility of the larger ring size calixarene with a larger hydrophobic surface area is likely to encourage 7C-7C stacking of the aromatic units of the benzyl and phenyl upper rim functionalities with the SWCNT surface.

Figure 3A:
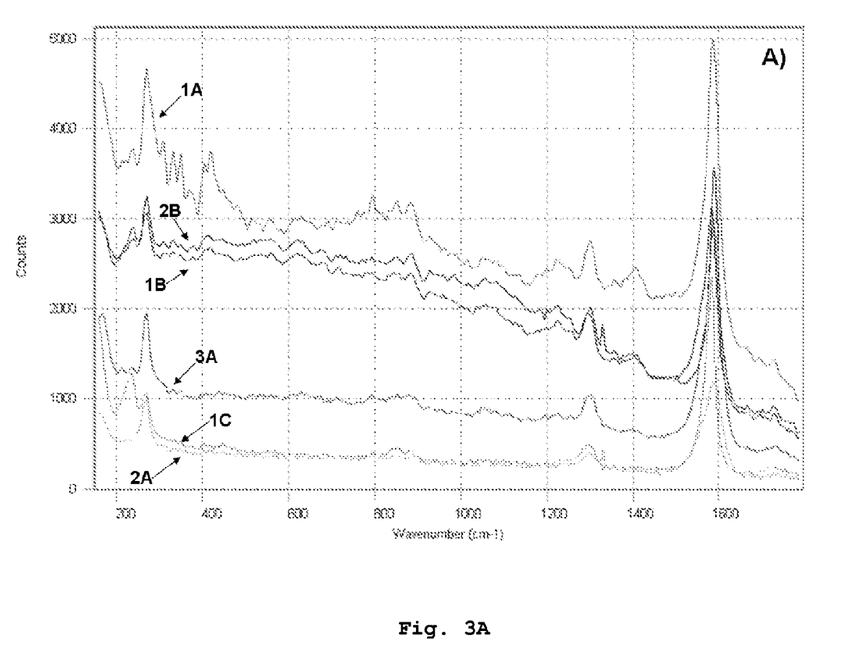
FIGS. 3A, 3B, and 3C show Raman spectra of calixarene-carbon nanotube complexes prepared in accordance with the present invention.

The results indicate that the peak width of the D-band at ~1590 cm$^{-1}$ has decreased significantly from 100 cm$^{-1}$ in the as-received SWCNTs to 20-40 cm$^{-1}$ (FWHM) in all trialed systems (FIGS. 3A & 4A). This peak width narrowing is attributed to the reduction of the amount of amorphous carbon in the sample, and indicates that all of the systems studied show a low binding affinity to amorphous carbon, and when coupled with centrifugal processing results in minimal amorphous carbon present in the aqueous supernatant. This supports the use of these water-soluble calixarenes in post-growth purification protocols.

It is important to measure the purity of the SWCNTs that have been solubilized using the calixarene host molecules. A method routinely utilized is the ratio from the intensity of the D-band to that of the G-band ($I_D/I_G$).[34] The lower the value of $I_D/I_G$ implies less disordered carbon attributed to the SWCNTs structure and hence an increased level of pristine SWCNTs. The as-received SWCNTs have a calculated $I_D/I_G$ ratio of 0.2131. The $I_D/I_G$ ratios are detailed in Table 2, with the hierarchy of $I_D/I_G$ ratios as follows 4B>3A>SWCNT as-received>1B>1A>2A>4C>2B>4A>1C. This shows that the majority of the calixarene systems increase the level of pristine SWCNTs in the supernatant, with the exception of 3A, 4B. The $I_D/I_G$ ratios for the 3A and 4B systems, albeit lower in purity, are relatively close to the as-received SWCNT ratio. Interestingly, the 3A and 4B systems reveal large G-band shifts, indicating significant surface interaction with the SWCNT surface. These systems may also bind to carbon particle impurities which can result in their disaggregation and lead to an increased D-band signal. This data further supports the use of the majority of these calixarene systems in post-growth purification protocols.

Figure 2:
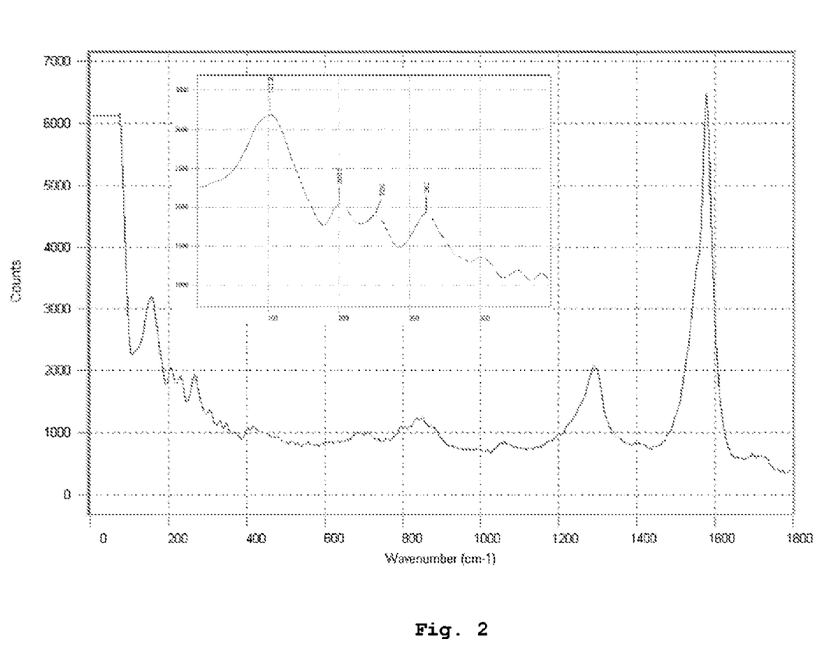
FIG. 2 shows a Raman spectrum of an as-received SWCNT.

The radial breathing mode (RBM) frequencies assigned within a Raman spectrum can provide direct information regarding the distribution of SWCNT diameters within a sample.[36] The relationship between the RBM frequency and the inverse nanotube diameter is well described in the literature:

$$\overline{v}_{RBM} = \frac{A}{d_t} + B$$

$$v_{RBM} = \frac{A}{d_t} + B$$

where $v_{RBM}$ is the RBM frequency in cm$^{-1}$, $d_t$ is the tube diameter in nm, and the parameters of A=223.5 cm$^{-1}$ nm and B=12.5 cm$^{-1}$ have been experimentally determined.[37] The Raman spectrum, including RBM region, for the as-received SWCNT is shown in FIG. 2. It should be noted that several reoccurring frequencies in the RBM range were identified and removed from the analysis. These could be contributed from either the aluminum foil, possible laser reflections and/or the sampling environment.

Figure 3B:
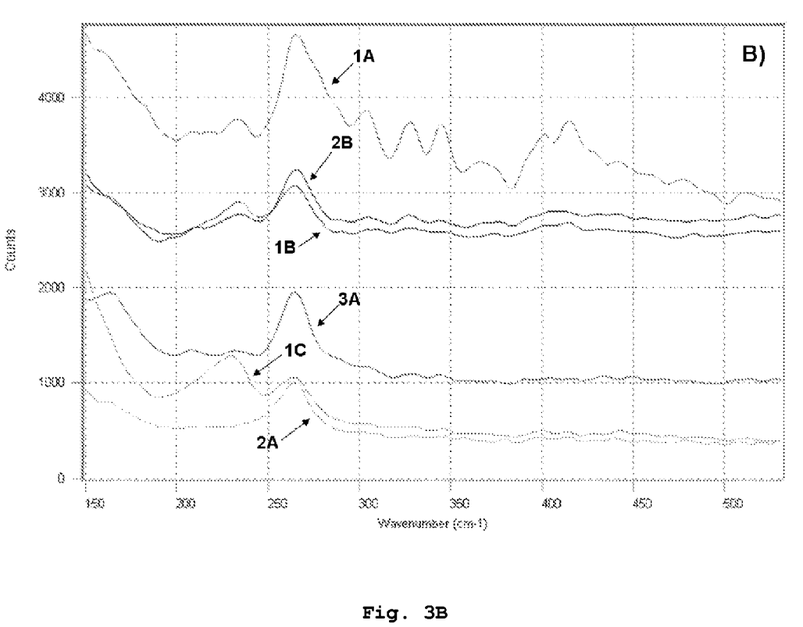
Figure 3C:
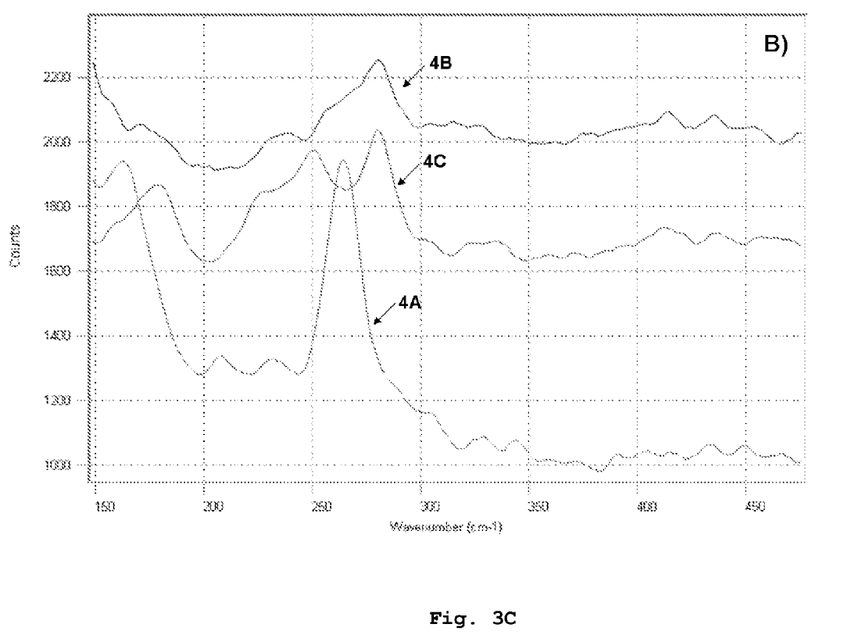

The dominant SWCNT diameters in the sample are 1.61 nm (151.25 cm$^{-1}$), 1.19 nm (200.49 cm$^{-1}$), 1.05 nm (225.99 cm$^{-1}$) and 0.90 nm (262.04 cm$^{-1}$) (FIG. 2). If a broad RBM band is observed it is possible that it is a superposition of a few Lorentzian components and could represent multiple diameter SWCNTs. This is possibly what is occurring with the 151.25 cm$^{-1}$ band, which is subsequently masking the larger diameter SWCNTs individual RBM bands. The spectra obtained from the p-phosphonated calixarene systems are shown in FIG. 3A & FIG. 3B. The p-sulfonated calixarene systems spectra are shown in FIG. 3C.

TABLE 3

Calculated SWCNT diameters present based on RBM frequencies in the Raman spectra.

| Sample | Calculated SWCNT diameter distribution (nm)[a] |
|---|---|
| As-received SWCNTs | 1.61, 1.19, 1.05, 0.89 |
| 1A | 1.01, 0.89 |
| 1B | 1.01, 0.89 |
| 1C | 1.04, 0.89 |
| 2A | 0.89 |
| 2B | 1.00, 0.89 |
| 3A | 1.00, 0.89 |
| 4A | 1.01, 0.89 |
| 4B | 0.91, 0.89 |
| 4C | 1.35, 1.04, 0.89 |

[a]SWCNT diameter relating to the most intense band is italicized.

A summary of the calculated SWCNT diameters present in the supernatants in each system is tabulated (Table 3). Firstly, the data supports the previous findings on solubilization of the SWCNTs. The data also indicates that there is selective uptake of particular diameter SWCNTs, which is highly dependent on the nature of the calixarene. In the majority of the supernatants the most intense band can be attributed to SWCNT with a diameter of 0.89 nm (ca. 262 cm$^{-1}$). Interestingly, this SWCNT diameter is not the most abundant in the as-received SWCNT sample (FIG. 2), yet this diameter seems to be efficiently solubilized, with the uptake in solution of larger diameter tubes limited.

As previously mentioned the smaller diameter SWCNTs were more readily solubilized into aqueous media. However, the data indicates that there are larger SWCNT diameters solubilized when using 4B (1.55 & 1.42 nm), 4C (1.35 nm). In the case of 4B & 4C involving the 'extended arm' sulfonated calix[8]arenes, the large G-band shifts indicate strong nanotube surface interactions. This suggests a different type of interplay with the SWCNT surface, in solubilizing the larger diameter SWCNTs. This is consistent with the increased conformational flexibility of the larger ring size calixarene.

Data in Table 3 also indicate that 1C and 2A are unique in regard to SWCNT solubilization. 1C shows the ability to preferentially bind to 1.04 nm (ca. 228 cm$^{-1}$) diameter SWCNTs, with the band having the greater RBM intensity. This diameter represents the smallest SWCNT diameter population in the as-received SWCNTs (FIG. 2). In contrast, 2A only solubilizes SWCNTs with a diameter 0.89 nm (ca. 264 cm$^{-1}$). These two systems not only significantly increase the purity of the SWCNTs (Table 2), they can also be utilised to preferentially solubilize SWCNTs of a specific diameter.

With the SWCNT diameter distribution in both the as-received SWCNT sample and the different calixarene system supernatants, it is now possible to calculate integers of assignment (Table 4)

$$d_t = a(n^2+m^2+nm)^{1/2}/\pi$$

where $a=0.249$ nm (due to $a=\sqrt{3}a_{c-c}=0.249$ nm [$a_{c-c}=0.142$ nm]) and the integers (n,m) define the structure of a SWCNT in terms of its diameter and chiral angle. Furthermore, following the topographical assignment, the electronic nature of each specified nanotube topology can be determined (Table 4). There are three possible electronic assignments, 1) quasi-metallic SWCNT with $|n-m|=3q$; 2) metallic SWCNT with $n=m$ and 3) semiconducting SWCNT with $|n-m|=3q\pm1$, where q is an integer.

TABLE 4

Observed RBM bands in the as-received SWCNTs and calixarene system supernatants with topographical and electronic assignment.

| Observed RBM band (cm$^{-1}$) ± 1 | Calculated SWCNT Diameter (nm) | Assignment (n, m) | Semiconducting (S) or Metallic (M) |
|---|---|---|---|
| 264 | 0.89 | (10, 2) | S |
| 257 | 0.91 | (11, 1) | S |
|  |  | (9, 4) | S |
| 235 | 1.00 | (12, 1) | S |
| 232 | 1.01 | (11, 3) | S |
| 228 | 1.04 | (12, 2) | S |
|  |  | (9, 6) | M |
| 226 | 1.05 | (10, 5) | S |
| 200 | 1.19 | (15, 0) | S |
| 178 | 1.35 | (15, 2) | S |
|  |  | (14, 5) | M |
| 151 | 1.61 | (18, 4) | S |

From the chiral assignment and subsequently the electronic nature of the SWCNTs in the supernatants (Table 4), it is possible to comment on the preferential solubilization of semiconducting and metallic SWCNTs. The majority of the SWCNTs analysed are semiconducting in nature, which is expected from using a 785 nm excitation wavelength, where excitation is primarily resonant with the v2→c2 transitions. In relation to the p-phosphonated calixarenes, all systems preferentially solubilized 0.89 nm, (10,2)—semiconducting SWCNTs based on RBM intensities. For the 1C system, while still solubilizing 0.89 nm SWCNTs, solubilization of the 1.04 nm, (12,2) semiconducting or (9,6) metallic SWCNTs occurs. This is the only p-phosphonated calixarene to bind to metallic SWCNTs. Most p-phosphonated systems solubilize two to three different diameter SWCNTs, whereas 2A only solubilized 0.89 nm (10,2) semiconducting SWCNTs. This selective binding to specific chiral SWCNTs has significant implications for post-growth purification and application selective processing for many current and future applications, in particular nano-electronics.

In relation to the electronic nature of the solubilized SWCNTs the results obtained from the p-sulfonated calixarene systems were similar to the p-phosphonated calixarene systems. However, it is interesting to note that 4C preferentially binds two different diameter metallic SWCNTs, along with the typical 0.89 nm SWCNTs. The intensities of these respective RBM bands are relatively similar which suggests that there is an enrichment of metallic SWCNTs in the supernatant for this system.

UV-Visible Spectrophotometry

In a recent study, UV-visible absorbance spectrophotometry was used to determine the concentration of SWCNTs in aqueous dispersions. The absorption peak at 273 nm is a signature of the surface π-plasmon excitation of dispersed SWCNTs. The supernatants obtained for the different calixarene systems, in this study, were analysed using this technique. In the majority of the systems slight increases in absorbance at the 273 nm peak were seen, when compared to solutions only containing the calixarene. However, these results are deemed inconclusive as the π-plasmon surface excitations of the calixarene adsorb strongly in the 273 nm region and it is possible the contribution from the SWNTs has been masked.

Transmission Electron Microscopy

Transmission Electron Microscopy (TEM) was utilised to assess the residues of the supernatants to give information on the solubilization characteristics and also reveal possible packing arrangement in the solid state that may relate to arrangement in the solubilized phase. TEM was carried out on the supernatants of the calixarene systems, with 1C results detailed in FIGS. 5 & 6.

Figure 5:
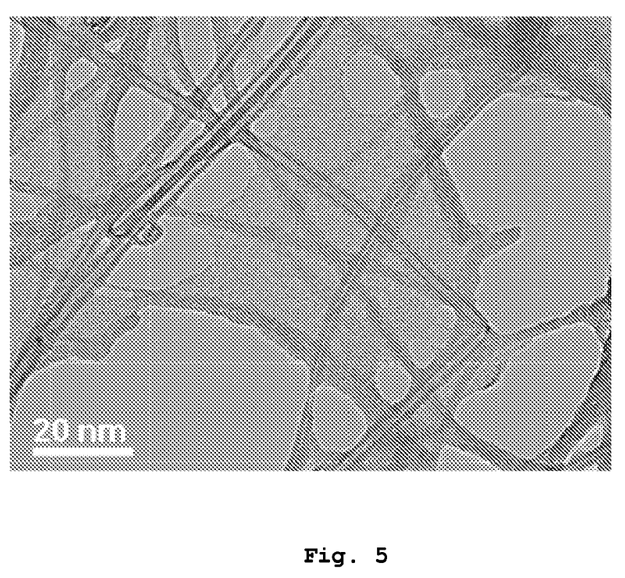
FIG. 5 shows a transmission electron microscopy (TEM) image illustrating a plurality of discrete carbon nanotubes coated with calixarene in accordance with the present invention.
Figure 6:
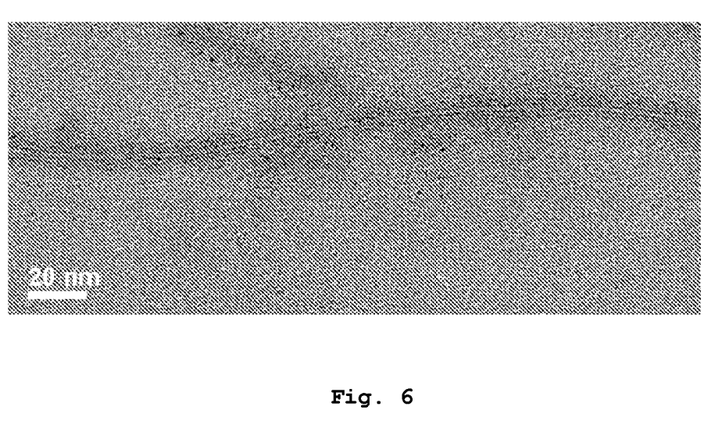
FIG. 6 shows a TEM image of a single carbon nanotube complexed with calixarene in accordance with the present invention.

The TEM image in FIG. 5 illustrates the typical structures observed on the grid, where networks of SWCNTs can be seen scattered with amorphous coatings of the calixarene sheathing the SWCNTs. As expected the SWCNTs are observed to be individual (FIG. 6), indicating the disruption of Van der Waals forces between SWCNT bundles and subsequent self assembly of the calixarene around a SWCNT surface for the effective solubilization into aqueous media. These results provide support for the increase in pristine SWCNT purity (Table 2). Energy dispersive X-ray analysis (EDX) has also been carried out on the sample with no peaks attributed to any remaining iron catalyst particles, further supporting the use of these systems for post-growth purification.

It is to be understood that, although prior art use and publications may be referred to herein, such reference does not constitute an admission that any of these form a part of the common general knowledge in the art, in Australia or any other country.

For the purposes of this specification it will be clearly understood that the word "comprising" means "including but not limited to", and that the word "comprises" has a corresponding meaning.

Numerous variations and modifications will suggest themselves to persons skilled in the relevant art, in addition to those already described, without departing from the basic inventive concepts. All such variations and modifications are to be considered within the scope of the present invention, the nature of which is to be determined from the foregoing description.

The invention claimed is:

1. A method of separating at least one carbon nanotube having a desired diameter and/or chirality from a mixture of carbon nanotubes having different diameters and/or chiralities comprising:

(a) selecting a calixarene of formula (I):

wherein n ≧4; X is $PO_3H_2$, $R_a$—$PO_3H$, $SO_3H$, or $R_a$—$SO_3H$; Y is $R_b$, OH, or $OR_b$; and $R_a$ and $R_b$ are independently selected from the group consisting of optionally substituted alkyl, optionally substituted aryl, optionally substituted arylene alkyl and optionally substituted alkylene aryl;

(b) combining the mixture of carbon nanotubes with the selected calixarene of step (a), in an aqueous solvent, to produce an aqueous supernatant containing the carbon nanotube(s) having the desired diameter and/or chirality; and (c) separating the aqueous supernatant of step (b) containing the carbon nanotube(s), from a residue comprising the remaining carbon nanotubes of the mixture.

2. The method according to claim 1, wherein the calixarene of formula (I) and the carbon nanotube(s) contained in the aqueous supernatant form a complex.

3. The method according to claim 1, wherein the carbon nanotube(s) that are contained in the aqueous supernatant are isolated by evaporation of the aqueous solvent.

4. The method according to claim 1, wherein the carbon nanotube(s) contained in the residue are isolated by decanting off the aqueous solvent or filtering out the residue.

5. The method according to claim 2, wherein the carbon nanotube(s) in the complex have diameters in the range of 0.89 nm-1.35 nm.

6. The method according to claim 5, wherein the carbon nanotube(s) have diameters in the range of 0.89-1.04 nm.

7. A method of separating at least one semiconducting carbon nanotube or at least one metallic carbon nanotube from a mixture of carbon nanotubes comprising:

(a) selecting a calixarene of formula (I):

(I)

wherein n ≧4; X is $PO_3H_2$, $R_a$—$PO_3H$, $SO_3H$, or $R_a$—$SO_3H$; Y is $R_b$, OH, or $OR_b$; and $R_a$ and $R_b$ are independently selected from the group consisting of optionally substituted alkyl, optionally substituted aryl, optionally substituted arylene alkyl and optionally substituted alkylene aryl;

(b) combining the mixture of carbon nanotubes, in an aqueous solvent, to produce an aqueous supernatant containing either the metallic carbon nanotube(s) or semi-conducting carbon nanotube(s); and (c) separating the aqueous supernatant of step (b) containing either the metallic carbon nanotube(s) or semi-conducting carbon nanotube(s), from a residue comprising the remaining nanotubes of the mixture.

8. The method according to claim 7, wherein the calixarene of formula (I), and either the metallic carbon nanotube(s) or the semi-conducting carbon nanotube(s), contained in the aqueous supernatant form a complex.

9. The method according to claim 7, wherein either the metallic carbon nanotube(s) or the semi-conducting carbon nanotube(s) that are contained in the aqueous supernatant are isolated by evaporation of the aqueous solvent.

10. The method according to claim 7, wherein the carbon nanotube(s) contained in the residue are isolated by decanting off the aqueous solvent or filtering out the residue.

11. A method of separating impurities from a mixture of carbon nanotubes comprising the steps of:

(a) combining in an aqueous solvent, the mixture of carbon nanotubes with at least one calixarene of formula (I):

(I)

wherein n ≧4; X is $PO_3H_2$, $R_a$—$PO_3H$, $SO_3H$, or $R_a$—$SO_3H$; Y is $R_b$, OH, or $OR_b$; and $R_a$ and $R_b$ are independently selected from the group consisting of optionally substituted alkyl, optionally substituted aryl, optionally substituted arylene alkyl and optionally substituted alkylene aryl to produce an aqueous supernatant containing the nanotubes and a residue comprising the impurities; and (b) separating the aqueous supernatant of step (a) from the residue containing the impurities of the mixture.

12. The method according to claim 11, wherein the nanotubes contained in the aqueous supernatant are present as a complex with the at least one calixarene of formula (I).

13. The method according to claim 11, wherein the impurities comprise amorphous carbon and metal catalysts.

\* \* \* \* \*